(12) United States Patent
Vargas

(10) Patent No.: US 6,206,690 B1
(45) Date of Patent: Mar. 27, 2001

(54) ORTHODONTIC APPLIANCE AND METHODS OF INSTALLATION AND REMOVAL

(75) Inventor: John G. Vargas, Whittier, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/415,867

(22) Filed: Oct. 8, 1999

(51) Int. Cl.⁷ .................................................. A61C 7/12
(52) U.S. Cl. ..................................................... 433/9; 433/8
(58) Field of Search ............................. 433/8, 9, 10, 16, 433/17

(56) References Cited

U.S. PATENT DOCUMENTS

| | | | |
|---|---|---|---|
| 4,595,598 | * 6/1986 | De Luca et al. | 433/9 |
| 4,927,360 | * 5/1990 | Pospisil | 433/9 |
| 4,936,773 | * 6/1990 | Kawaguchi | 433/9 |
| 5,094,614 | 3/1992 | Wildman | 433/14 |
| 5,439,378 | 8/1995 | Damon | 433/8 |
| 5,707,231 | * 1/1998 | Watt et al. | 433/9 |
| 6,053,729 | * 4/2000 | Brehm et al. | 433/9 |

* cited by examiner

Primary Examiner—Ralph A. Lewis
(74) Attorney, Agent, or Firm—Wood, Herron & Evans, L.L.P.

(57) ABSTRACT

An orthodontic bracket having opposite nonparallel surfaces and further incorporating one or more gripping portions to provide stability in gripping and handling. The gripping portion or portions may be formed as various types of small notches or shelves in the bracket body and preferably enable gripping to take place on opposite parallel surfaces even though surrounding surfaces are nonparallel and may be convergent. Methods of installation and removal involve gripping the appliance with a tool having movable jaws with at least one jaw engaging a gripping portion.

19 Claims, 4 Drawing Sheets

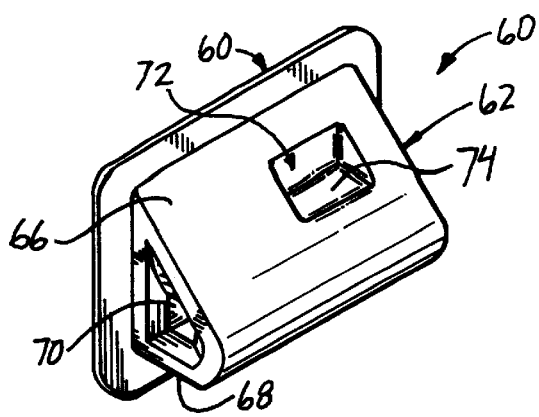
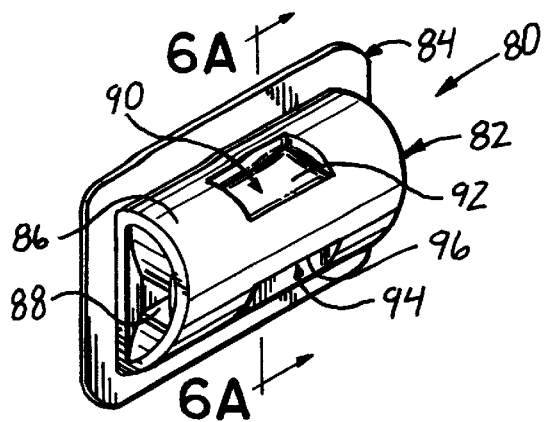
FIG.5  FIG.6
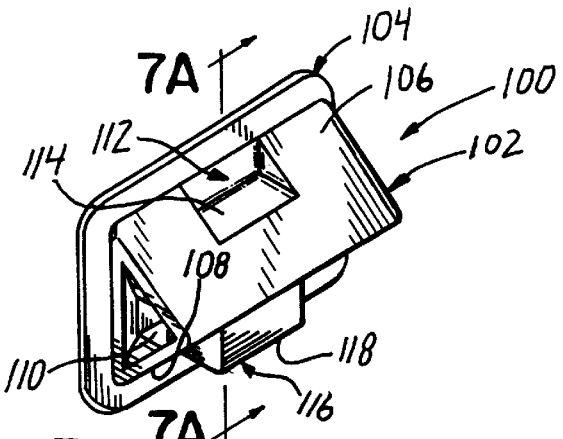
FIG.7
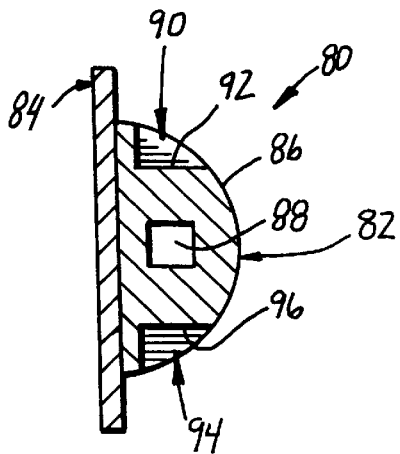
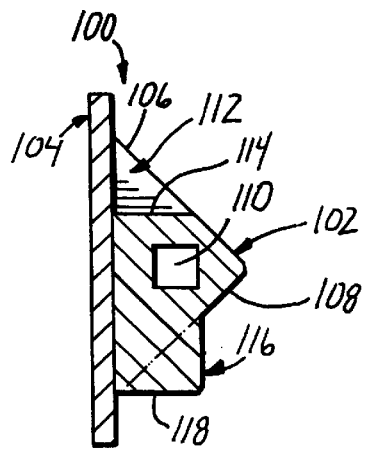
FIG. 6A  FIG.7A

ORTHODONTIC APPLIANCE AND METHODS OF INSTALLATION AND REMOVAL

TECHNICAL FIELD

The present invention relates to orthodontic appliances, such as brackets and buccal tubes for fixation to the teeth of a patient. More particularly, the invention relates to such appliances with non-parallel opposite surfaces adapted to be gripped by a tool during installation and/or removal procedures.

BACKGROUND OF THE INVENTION

Improperly positioned teeth may be forced into desired positions through the use of a flexible wire, referred to by orthodontists as an archwire, and a series of appliances affixed to respective upper and lower teeth. The appliances currently take the form of specialized brackets and buccal tubes formed from suitable metallic or ceramic or plastic material. The orthodontist typically adheres the appliances to the teeth with an adhesive, although other fixation methods are known as well. Each appliance includes a slot or a hole to receive and control the position of the archwire.

The design of orthodontic appliances involves the balancing of several considerations. The appliance must adequately retain and position the archwire and further allow for adjustments to the archwire. Preferably, appliances are compatible with other dental attachments with minimal complexity and are strong yet compact. The most common bracket design is the so-called tie-wing bracket. This bracket includes a slot for insertion of the archwire and a plurality of projections referred to as wings. After the archwire is set in the slot of the bracket, either a tie wire or an O-ring is affixed beneath the wings and over the archwire at each end of the archwire slot. The tie-wing bracket is a simple design and provides excellent control of the archwire. Brackets of this type typically have parallel upper and lower surfaces of adequate size to be easily gripped with conventional orthodontic pliers. However, some orthodontic appliances are generally tubular in shape or otherwise have nonparallel, opposite surfaces. These appliances include buccal tubes used on rear molars to anchor and hold the archwire ends in proper alignment.

In one prior buccal tube design, for example, one outer surface slopes downwardly from a position close to the base or tooth mounting surface and an opposite outer surface extends essentially perpendicular from the base. A small gripping ledge is contained on the body of the buccal tube and intersects the sloped surface. In addition to facilitating patient comfort, one of the main functions of the sloping surface is to deflect food particles which may become lodged between respective buccal tubes of the upper and lower teeth as the patient chews food, especially hard foods such as hard candy, etc. Unfortunately, the sloping surface also impedes the ability of the orthodontist to grasp the buccal tube with a pair of conventional pliers during installation or removal procedures. The small gripping ledge on the body of the buccal tube is not easily grasped at all times and the orthodontist may therefore experience "shoot-out" of the buccal tube from the tool as one of the gripping jaws of the tool slides down the sloping surface.

While it would be desirable to continue providing one or more sloping surface in many orthodontic appliances, it would also be desirable to provide a orthodontic appliance, such as a buccal tube or other orthodontic bracket or appliance, with better gripping ability despite the presence of opposite, nonparallel appliance surfaces.

SUMMARY OF THE INVENTION

The present invention is therefore directed to an orthodontic appliance having nonparallel opposite surfaces, such as upper and lower surfaces, but having at least one specialized portion that may be securely gripped with an orthodontic tool during installation. The appliance generally includes a body with a plurality of outer surfaces. One surface is a mounting surface or base which is affixed against a tooth, such as with an adhesive or in another suitable manner. The body also includes a passage, such as an open-ended hole or an open channel, for receiving an archwire. Two opposed outer surfaces are nonparallel in that at least one of the outer surfaces generally slopes toward the other. The slope may be angular and planar or may be rounded. Other nonparallel configurations may derive benefit from this invention as well. In accordance with the present invention, a gripping portion is located on the body such that it intersects one of the nonparallel outer surfaces, such as the sloping outer surface. This portion creates a gripping surface which, in conjunction with the opposite outer surface, is used to grasp the body with much greater stability than previous appliance configurations having nonparallel opposite surfaces.

In one particular example, the upper outer surface of a buccal tube, as used on a lower molar, begins generally at an upper edge and slopes downward. The slope of this surface aids in patient comfort and causes food particles to be deflected away from the tooth and the corresponding upper buccal tube. The gripping portion may comprise at least two alternative forms. First, a notch or recess may be formed into the sloping outer surface. Second, the gripping portion may take the form of a small shelf which projects slightly outward from the sloping outer surface. Each form of the gripping portion creates a generally parallel gripping surface relative to the opposite gripping surface which may or may not also be formed as a notch or shelf. Ideal gripping is achieved when the gripping surfaces are parallel. However, the gripping portion of one nonparallel surface may be only substantially parallel with an opposite gripping surface and still achieve the objective of this invention.

A method of using the appliance is also contemplated by the present invention. Generally, an orthodontic gripping tool having movable jaws is positioned with its jaws on opposite sides of the appliance. The jaws are then closed and thus become seated on the body of the appliance. Seating is accomplished on a first gripping surface portion of one nonparallel surface and the opposing gripping surface which may or may not be another gripping surface portion formed on an otherwise nonparallel surface relative to the first gripping surface portion. The compressive force exerted by the tool is increased to ensure the appliance is firmly held. Then, the appliance is directed into the patient's mouth and affixed to the patient's tooth. The gripping tool is then released from the appliance after the appliance has been fixed to the tooth. A similar method, which is essentially the reverse of the installation method, may be used during a removal procedure.

Other features, objects and advantages of the invention will become more readily apparent to those of ordinary skill in the art upon review of the following detailed description of the preferred embodiments, taken in conjunction with the accompanying drawings.

BRIEF DESCRIPTION OF DRAWINGS

FIG. 5 is a perspective view of another alternative embodiment of the present invention.

FIG. 6 is a perspective view of another alternative embodiment of the present invention.

FIG. 6A is a cross sectional view taken along line 6A—6A of FIG. 6.

FIG. 7 is a perspective view of another alternative embodiment of the invention.

FIG. 7A is a cross sectional view taken along line 7A—7A of FIG. 7.

DETAILED DESCRIPTION OF THE PREFERRED EMBODIMENTS

The advantages of the present invention and its preferred embodiments described herein are best revealed by briefly considering the prior art. It will be appreciated that terms of orientation, such as "upper", "lower" and other similar terminology, are used for purposes of clarity with respect to the illustrative drawings. These terms are not meant to be limiting in any manner as orientations of orthodontic appliances may vary in practice. It should also be understood that, although the preferred and alternative embodiments of the invention are specifically directed to buccal tubes, the inventive concepts herein may be applied to other forms of orthodontic appliances exhibiting similar problems and deriving similar benefits from the inventive concepts.

Figure 1:
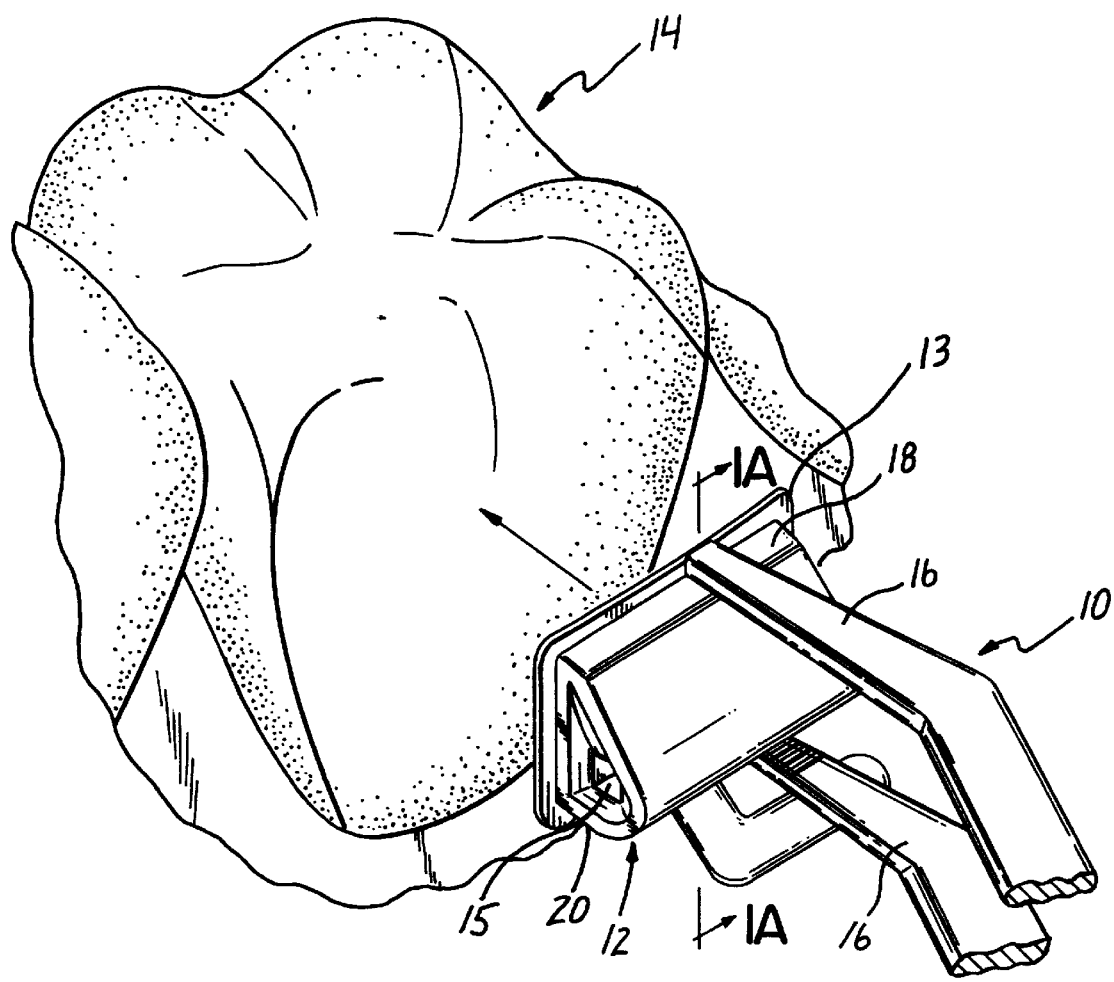
FIG. 1 is a perspective view showing an orthodontic appliance in the form of a buccal tube of the prior art being applied to a tooth.
Figure 1A:
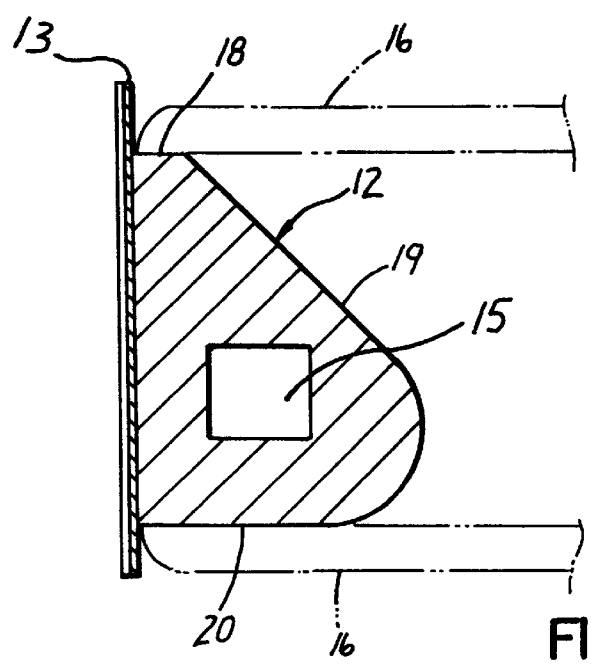
FIG. 1A is a cross-sectional view taken along line 1A—1A of FIG. 1 and showing the orthodontic gripping tool engaging the prior art buccal tube.

Referring first to FIG. 1, an orthodontic gripping tool 10 is shown as typically used to position a buccal tube body 12 and attached base 13 on a tooth 14. A hole 15 is provided for an archwire (not shown). The gripping tool 10 has jaws 16 which seat upon a narrow upper ledge 18 of the body 12 and a parallel lower surface 20. The upper ledge 18 must be as narrow as possible to prevent undesirable contact with food during chewing. The engagement of jaws 16 on upper ledge 18 and lower outer surface 20 is shown in cross section in FIG. 1A. As especially evident from FIG. 1A, upper ledge 18 provides substantially less area for gripping than lower surface 20. This can cause the body 12 to shoot out of jaws 16 during installation procedures. Particularly, the upper jaw 16 can quickly slide down angled surface 19, which converges toward surface 20, if the grip with narrow ledge 18 is lost.

Figure 2:
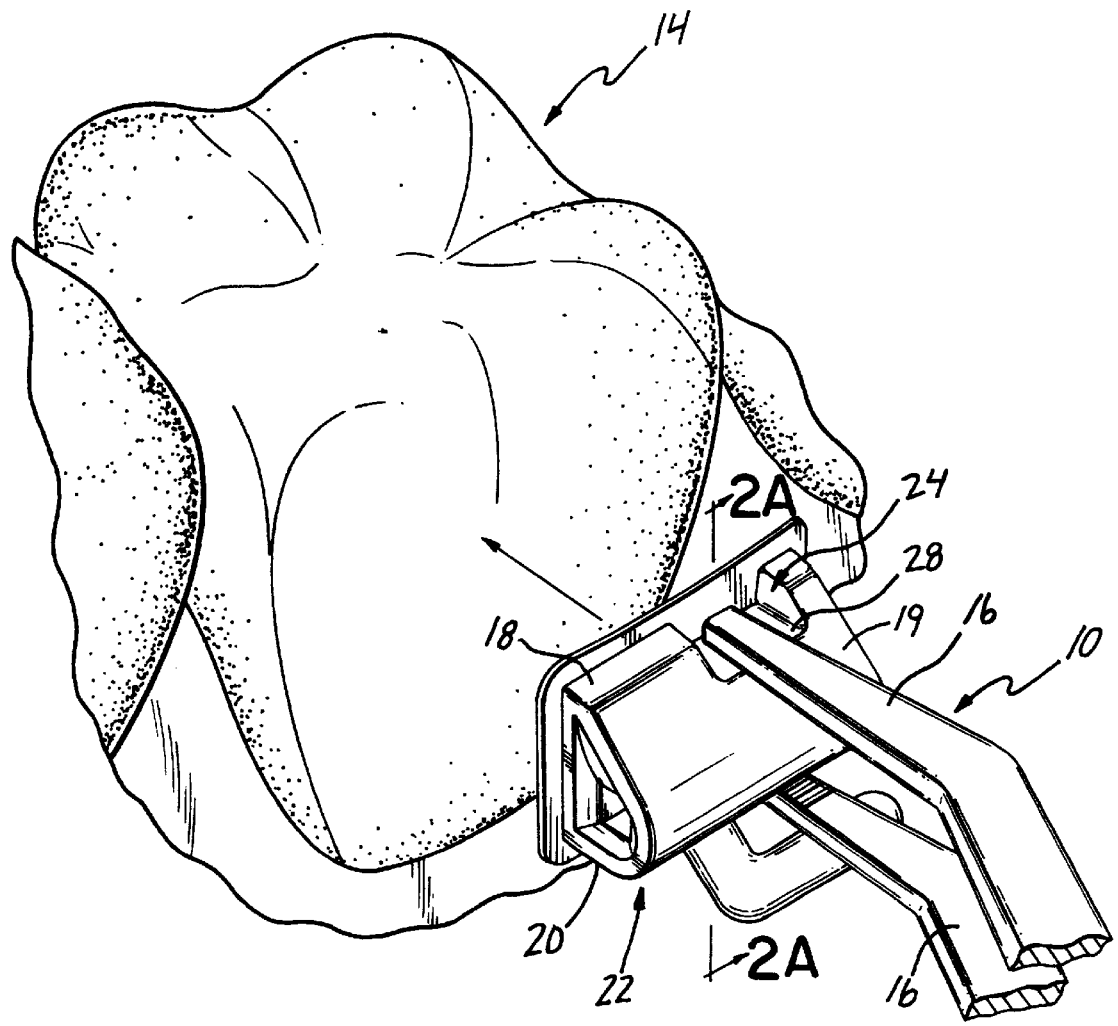
FIG. 2 is a perspective view showing an orthodontic appliance in the form of a buccal tube of the present invention being applied to a tooth.
Figure 2A:
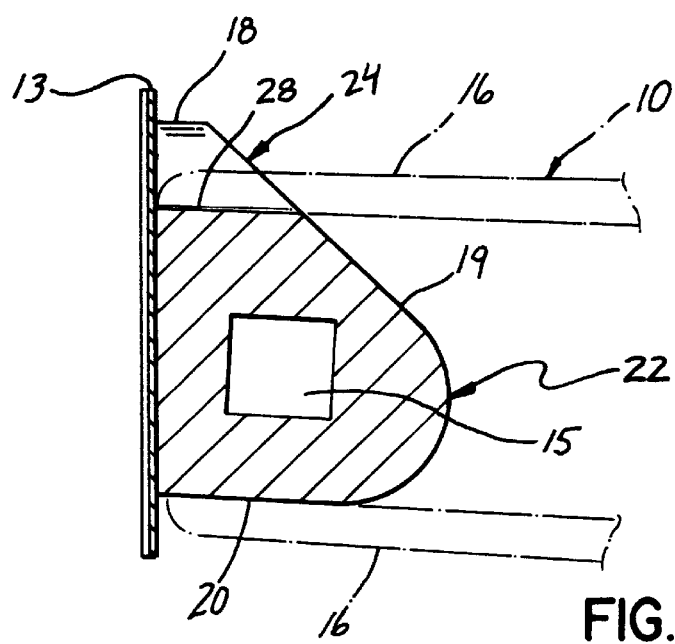
FIG. 2A is a cross-sectional view taken along line 2A—2A of FIG. 2 and showing the orthodontic gripping tool engaging the preferred buccal tube.
Figure 3:
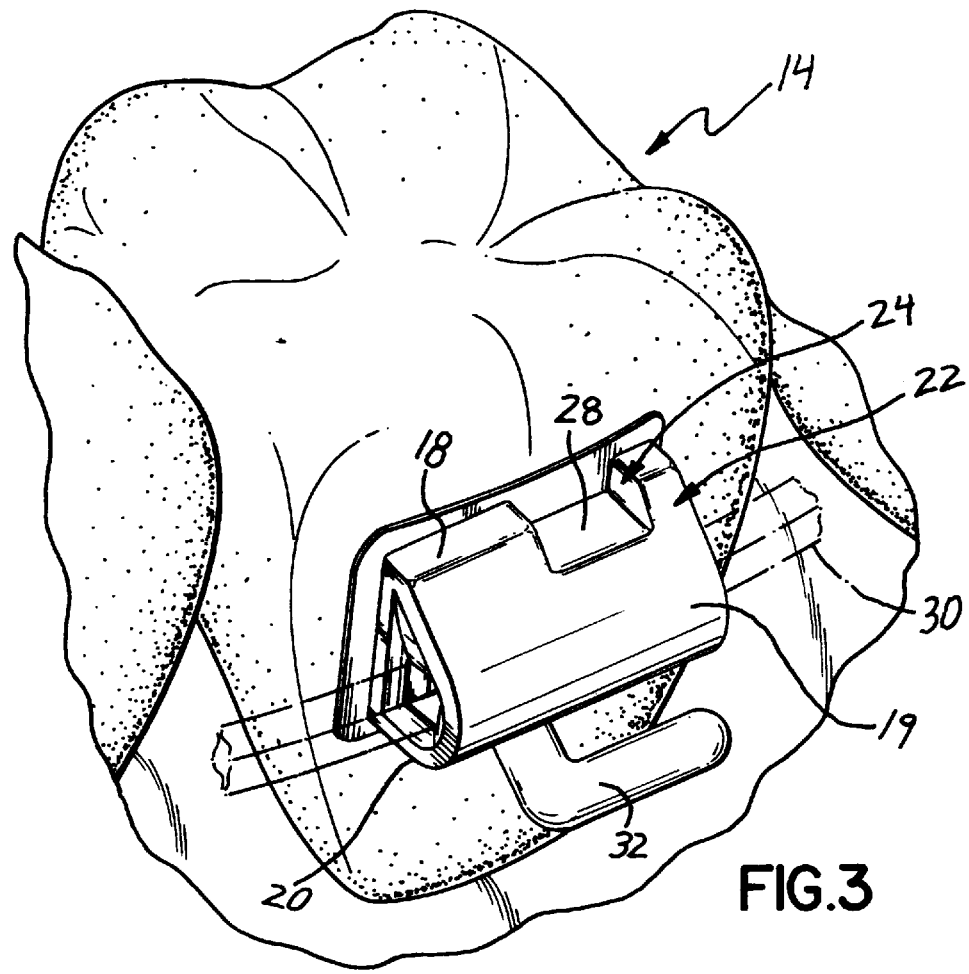
FIG. 3 is a perspective view showing the preferred buccal tube mounted on a tooth.

An orthodontic appliance constructed according to the present invention helps minimize the shoot-out problem mentioned above while also maintaining the provision of nonparallel upper and lower surfaces, for example, in cases in which it is necessary or desirable to have at least one rounded or angled surface sloping toward an opposite surface. Such a sloped surface can aid patient comfort and minimize forceful contact with food during chewing. Turning to FIGS. 2, 2A and 3, the preferred embodiment of the invention is shown mounted to tooth 14, with other like numerals in these figures representing like structure or elements in FIGS. 1 and 1A. A buccal tube 22 is shown and incorporates a gripping portion 24 which, in this case, comprises a notch. Notch 24 thereby forms an upper gripping surface 28. As FIGS. 2 and 2A illustrate, gripping tool 10 applies a compressive force on buccal tube 22 through jaws 16 which seat upon gripping surface 28 and the opposed lower surface 20.

Increased and more secure gripping force may be applied due to the extended gripping dimension, in a direction away from tooth 14, provided by surface 28. Surfaces 20 and 28 are at least substantially parallel to each other and thereby ensure positive gripping by tool 10. Gripping portion or notch 24 extends downwardly from the narrow upper ledge 18 and intersects angled surface 19. As further shown in FIG. 3, after buccal tube 22 is mounted on tooth 14, an archwire 30 may be inserted through buccal tube 22 in a conventional manner. As is also conventional, at least one auxiliary attachment 32 can form part of buccal tube 22 and may be used to hold auxiliary devices, such as rubber bands. Buccal tube 22, as well as other appliances formed in accordance with the invention, may be made of any suitable orthodontic material. As examples, these may include ceramic materials, metals such as stainless steel or titanium, or metal alloys.

Figure 4:
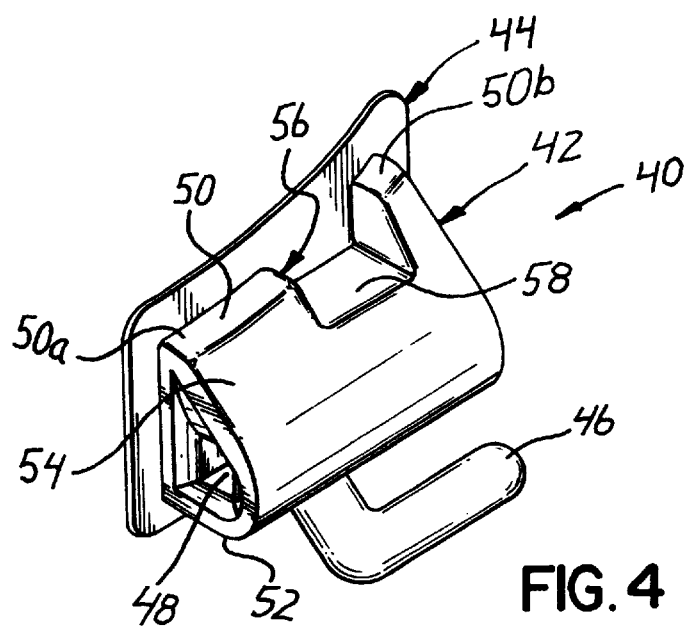
FIG. 4 is a perspective view showing another embodiment of the present invention.

Turning now to FIG. 4, an alternative embodiment of a buccal tube 40 includes a body 42 and a base 44 for attachment to a tooth. Buccal tube 40 may again include an auxiliary attachment 46 and a throughhole 48 for receiving an archwire. It will be appreciated that certain orthodontic appliances will not require a throughhole, but instead will utilize an open channel. Body 42 again includes a narrow upper ledge 50 and a lower surface 52. In this embodiment, however, ledge 50 includes a first end 50a which is at a different elevation than a second end 50b. In a conventional buccal tube of this shape, this creates a slope from one end 50b toward the other end 50a of ledge 50. For this reason, gripping with a conventional tool, such as tool 10 of FIG. 1, is even more difficult as the jaws of the tool will tend to slide downwardly on the sloped ledge 50. Thus, there is even a greater tendency for the tool to lose its grip on body 42 by having a jaw slide down on upper ledge 50 and subsequently move down angled surface 54. This embodiment again utilizes a notch 56 to solve this problem. Notch 56 extends downward from ledge 50 and intersects angled surface 54 at a wider gripping surface 58 thereby creating more gripping area for a tool of the general type shown in FIG. 1. Jaws 16 of tool 10 may securely grip body 42 by engaging surface 58 and the opposite, parallel surface 52.

FIG. 5 illustrates another alternative embodiment of a buccal tube 60 which is very similar to the embodiment of FIGS. 2–3, however, the upper narrow ledge 18 has been eliminated to further decrease the potential for undesirable contact with food during chewing. More specifically, buccal tube 60 includes a body 62 and a base 64 for attachment to a tooth 14 (FIG. 1). Upper angled surface 66 intersects with a lower surface 68 which is adapted to extend substantially normal to the outer surface of tooth 14 after attachment thereto. As is conventional, buccal tube 60 includes a throughhole 70 for receiving a conventional archwire. In accordance with the invention, a notch 72 is formed in the upper angled surface 66 in order that a gripping surface 74 is formed at least substantially parallel to lower surface 68. In this manner, a conventional tool 10 (FIG. 1) may be used to firmly grip surfaces 68, 74 during an installation or removal procedure.

FIGS. 6 and 6A illustrates another alternative configuration in which a buccal tube 80 generally includes a body 82 and a base 84. The body includes a generally rounded outer surface 86. Like the other appliance configurations disclosed and discussed herein, this would normally create gripping problems in that the generally sloped and converging upper and lower surface portions of the body 82 are nonparallel in a manner that promotes shoot-out problems. Body 82 again includes a conventional throughhole or archwire hole 88. In accordance with the invention, an upper notch 90 forming an upper gripping surface 92 is formed within body 82 along with an opposed lower notch 94 forming a lower gripping surface 96. As best shown in FIG. 6A, notches 90, 94 and, more specifically, parallel gripping surfaces 92, 96 form a gripping area on body 82 that may be securely and forcefully gripped with the jaws 16 of a conventional tool 10 (FIG. 1).

Turning now to FIGS. 7 and 7A, another alternative appliance configuration and gripping area configuration is shown. Specifically, a buccal tube 100 includes a body 102 and a base 104. Body 102 includes upper and lower angled surfaces 106, 108 converging toward one another. Alternatively, these surfaces 106, 108 may be rounded. Normally, this type of configuration would be virtually impossible to grip with conventional gripping tools, however, in accordance with the invention, a notch 112 formed with a gripping surface 114 is contained in upper surface 106 and a shelf 116 formed with a gripping surface 118 projects from lower angled surface 108. In this manner, gripping surfaces 114, 118 are formed at least substantially parallel to one another and provide a gripping area sufficiently sized to allow secure and forceful compressive gripping by a conventional tool, such as tool 10 (FIG. 1). It will be understood that other forms and/or combinations of gripping portions may be used in place of these specifically disclosed herein.

The methods of this invention are best illustrated with reference to FIGS. 2 and 2A. A method of installing an orthodontic appliance, such as buccal tube 22 formed in accordance with the invention, includes positioning one of the jaws 16 of a gripping tool 10 on gripping surface 28 of notch 24 and positioning the other of the jaws 16 on the opposite surface 20. Compression may then be applied to jaws 16 by the orthodontist to securely grip buccal tube 22 as it is directed into the patient's mouth toward tooth 14. Base 13 of buccal tube 22 is then affixed to tooth 14, such as with a conventional orthodontic adhesive. Once the buccal tube 22 is adequately adhered to tooth 14, jaws 16 may be released and the orthodontist may move on to apply the next appliance. Removal of buccal tube 22 may involve similar steps as described above. For example, orthodontists may remove appliances by heating the appliance sufficiently to soften the adhesive between base 13 and tooth 14. When the adhesive is sufficiently softened, tool 10 and, specifically, jaws 16 may again be used to engage surfaces 20, 28 to compressively grip buccal tube 22 and then remove buccal tube 22 from tooth 14. It will further be appreciated that the remaining embodiments of this invention, as well as other orthodontic appliances configured in accordance with the invention, may be installed and removed in a similar manner by engaging the gripping portion or portions of the appliance with a suitable plier-type orthodontic tool such as tool 10.

While the present invention has been illustrated by a description of the preferred embodiment and while this embodiment has been described in some detail, it is not the intention of the Applicant to restrict or in any way limit the scope of the appended claims to such detail. Additional advantages and modifications will readily appear to those skilled in the art. Many different orthodontic appliance configurations may benefit from the inventive concepts disclosed herein. As only one of many alternatives, appliances of this invention may also including weldable bases, i.e., for welding to bands or crowns. This has been a description of the present invention, along with the preferred methods of practicing the present invention as currently known. However, the invention itself should only be defined by the appended claims, wherein I claim:

What is claimed is:

1. An orthodontic appliance mountable on a tooth, said appliance comprising:
    a body with an open-ended, elongate hole having first and second openings at opposite ends and adapted to receive and surround an archwire therein,
    a first outer surface on said body, said first outer surface having an upper edge generally parallel to said elongate hole, and said first outer surface intersecting said upper edge and sloped generally downwardly from said upper edge,
    a second outer surface on said body, said second outer surface positioned opposite to said first outer surface and nonparallel to said first outer surface, and
    a gripping portion extending from said first outer surface below said upper edge, said gripping portion forming a gripping surface which is at least substantially parallel to said second outer surface such that a tool may grip the appliance between said gripping surface and said second outer surface.

2. An orthodontic appliance according to claim 1, wherein said gripping surface is parallel to said second outer surface.

3. An orthodontic appliance according to claim 1, wherein said gripping portion is a notch extending inwardly from said first outer surface.

4. An orthodontic appliance according to claim 1, wherein said gripping portion is a shelf extending outwardly from said first outer surface.

5. An orthodontic appliance according to claim 1, wherein said second outer surface comprises a notch in a generally sloping surface.

6. An orthodontic appliance according to claim 1, wherein said second outer surface comprises a shelf in a generally sloping surface.

7. An orthodontic appliance according to claim 1, wherein said appliance is a buccal tube.

8. A method of installing an orthodontic appliance on the tooth of a patient using a gripping tool having opposed and movable jaws, said appliance including a body with an open-ended, elongate hole having first and second openings at opposite ends and adapted to receive and surround an archwire therein, a first outer surface on said body, said first outer surface having an upper edge generally parallel to said elongate hole and said first outer surface intersecting said upper edge and sloped generally downwardly from said upper edge, a second outer surface on said body, said second outer surface positioned opposite to said first outer surface and nonparallel to said first outer surface, and a gripping portion extending from said first outer surface below said upper edge, said gripping portion forming a gripping surface which is at least substantially parallel to said second outer surface such that a tool may grip the appliance between said gripping surface and said second outer surface, wherein the method comprises:
    positioning one of said jaws on the gripping surface,
    positioning the other jaw on the opposite outer surface,
    moving the jaws together to apply compressive force to the appliance and thereby securely grip the appliance, directing the gripped appliance into the patient's mouth, and affixing the appliance to the patient's tooth.

9. The method of claim 8, wherein the opposite outer surface further comprises a gripping portion formed in a second generally sloping surface and the step of positioning the other jaw on the opposite outer surface further comprises:

positioning the other jaw on the gripping portion of the second generally sloping surface.

10. The method of claim 9, wherein the step of positioning the other jaw on the gripping portion of the second generally sloping surface further comprises:

positioning the other jaw in a notch formed in the second generally sloping surface.

11. The method of claim 9, wherein the step of positioning the other jaw on the gripping portion of the second generally sloping surface further comprises:

positioning the other jaw on a shelf extending from the second generally sloping surface.

12. The method of claim 8, wherein the gripping portion further comprises a notch that includes said gripping surface and the step of positioning said one jaw on the gripping surface further comprises:

positioning said one jaw in said notch.

13. The method of claim 8, wherein the gripping portion further comprises a shelf that includes said gripping surface and the step of positioning said one jaw on the gripping surface further comprises:

positioning said one jaw on said shelf.

14. A method of removing an orthodontic appliance on the tooth of a patient using a gripping tool having opposed and movable jaws, said appliance including a body with an open-ended, elongate hole having first and second openings at opposite ends and adapted to receive and surround an archwire therein, a first outer surface on said body, said first outer surface having an upper edge generally parallel to said elongate hole and said first outer surface intersecting said upper edge and sloped generally downwardly from said upper edge, a second outer surface on said body, said second outer surface positioned opposite to said first outer surface and nonparallel to said first outer surface, and a gripping portion extending from said first outer surface below said upper edge, said gripping portion forming a gripping surface which is at least substantially parallel to said second outer surface such that a tool may grip the appliance between said gripping surface and said second outer surface, wherein the method comprises:

positioning one of said jaws on the gripping surface, positioning the other jaw on the opposite outer surface, moving the jaws together to apply compressive force to the appliance and thereby securely grip the appliance, and removing the appliance from the patient's tooth.

15. The method of claim 14, wherein the opposite outer surface further comprises a gripping portion formed in a second generally sloping surface and the step of positioning the other jaw on the opposite outer surface further comprises:

positioning the other jaw on the gripping portion of the second generally sloping surface.

16. The method of claim 15, wherein the step of positioning the other jaw on the gripping portion of the second generally sloping surface further comprises:

positioning the other jaw in a notch formed in the second generally sloping surface.

17. The method of claim 15, wherein the step of positioning the other jaw on the gripping portion of the second generally sloping surface further comprises:

positioning the other jaw on a shelf extending from the second generally sloping surface.

18. The method of claim 14, wherein the gripping portion further comprises a notch that includes said gripping surface and the step of positioning said one jaw on the gripping surface further comprises:

positioning said one jaw in said notch.

19. The method of claim 14, wherein the gripping portion further comprises a shelf that includes said gripping surface and the step of positioning said one jaw on the gripping surface further comprises:

positioning said one jaw on said shelf.

* * * * *